United States Patent [19]
Foley

[11] Patent Number: 5,228,970
[45] Date of Patent: * Jul. 20, 1993

[54] GEL ELECTROPHORESIS CASSETTE WITH REMOVABLE STRIP

[75] Inventor: Brian D. Foley, Westford, Mass.

[73] Assignee: Millipore Corporation, Bedford, Mass.

[*] Notice: The portion of the term of this patent subsequent to Sep. 22, 2009 has been disclaimed.

[21] Appl. No.: 759,262

[22] Filed: Sep. 13, 1991

[51] Int. Cl.$^5$ .................. G01N 27/26; G01N 27/447; B01D 57/02
[52] U.S. Cl. .................. 204/299 R; 204/182.8
[58] Field of Search .................. 204/299 R; 220/270, 220/269, 271

[56] References Cited

U.S. PATENT DOCUMENTS

| | | | |
|---|---|---|---|
| 4,211,336 | 7/1980 | Helms | 220/270 |
| 4,434,908 | 3/1984 | French | 220/276 |
| 4,548,333 | 10/1985 | Kobayashi et al. | 220/270 |
| 4,929,329 | 5/1990 | Danby et al. | 204/299 R |

Primary Examiner—John Niebling
Assistant Examiner—John S. Starsiak, Jr.
Attorney, Agent, or Firm—Paul J. Cook; Andrew T. Karnakis

[57] ABSTRACT

A gel electrophoresis cassette is formed of two plates and two spacers between the plates which plates and spacers form a void volume for housing a gel. The spacers are positioned slightly inward of the edges of the plates to form a first and a second small space. A strip and an adhesive are positioned within the small space. When the strips are removed from the small spaces, the adhesive is torn and the plates can be opened manually.

15 Claims, 2 Drawing Sheets

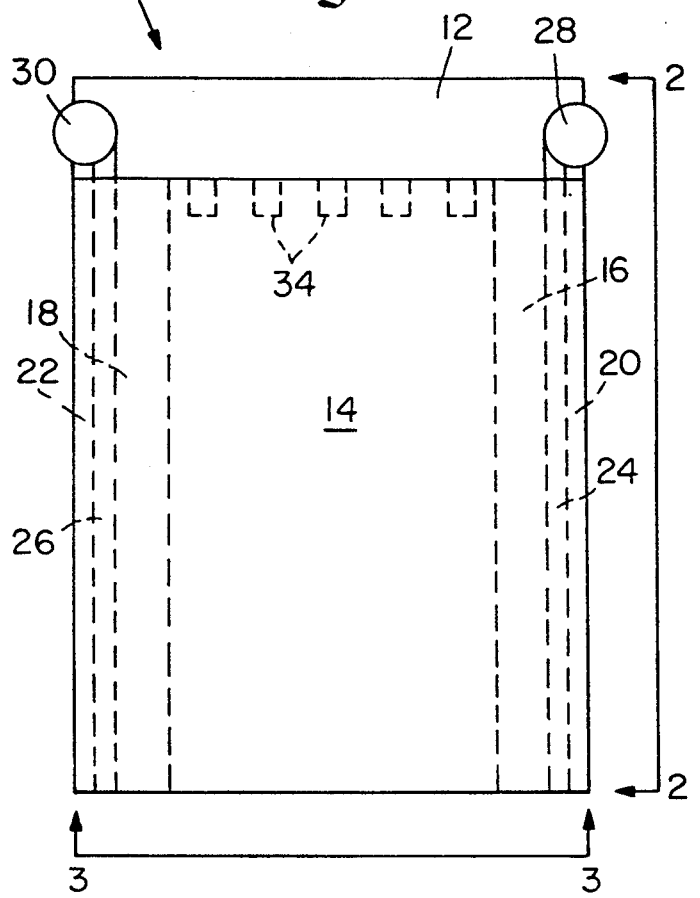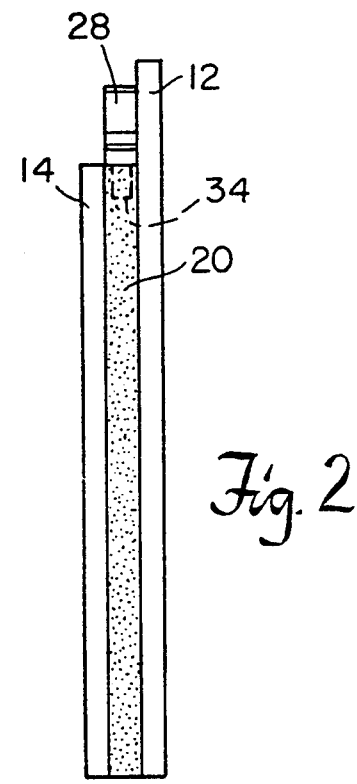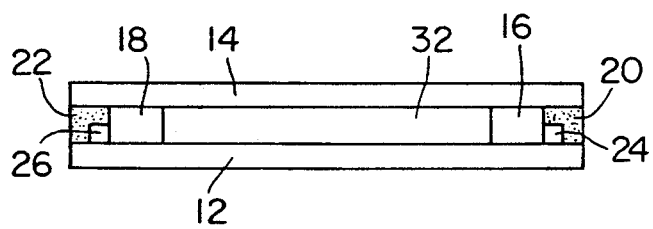

GEL ELECTROPHORESIS CASSETTE WITH REMOVABLE STRIP

BACKGROUND OF THE INVENTION

This invention relates to an electrophoresis cassette useful for conducting gel electrophoresis separations.

Electrophoresis is the resolution of a complex mixture of macromolecules on the basis of charge and/or size under the influence of an electric field and is a primary tool in analytical chemistry, used to separate complex mixtures of molecules such as proteins into their individual components. Electrophoretic analysis is based upon the fact that each molecule is characterized by a particular electrophoretic mobility under a given set of conditions. Macromolecules will migrate within a voltage gradient according to their net charge and will reach equilibrium at their isoelectric point at which their net mobility will be zero. For example, many proteins exhibit a net negative charge which is affected by the surrounding pH. When a mixture of proteins is placed in a support medium, such as a buffered gel, which is subjected to a voltage gradient, each component is caused to migrate through the support medium at its characteristic rate for that set of conditions. Electrophoretic mobility is a function of net charge, molecular weight, shape and a number of other factors which are controlled by experimental conditions.

It is common practice to conduct electrophoresis in a buffered gel positioned between two flat plates, usually transparent glass or plastic and separators which provide essential support for the gel. In order to provide accurate sample resolution, it is necessary that the gel composition be uniform and that the gel thickness be uniform. These conditions are necessary in order to avoid factors which affect molecular electrophoretic mobility other than the characteristics of the molecules being separated.

Presently, a cassette is produced wherein a void volume is formed between two plates separated by two separators. A suitable separation gel medium such as agarose or a polyacrylamide is poured, in liquid form, into the void volume and allowed to gel therein. During formation of the gel, the two plates are compressed to the separators with tape or clamps to prevent leakage of the gel material from the void volume and to assure a uniform distance between the plates, which, in turn, assures a uniform gel thickness.

In use, the cassette is positioned between two buffer solutions after the sample or samples have been placed on one gel surface. A voltage is applied between the buffers which causes the samples to migrate within the gel. Upon completion of sample preparation, the gel is separated from the plates for analysis. When using tape or an adhesive to secure the plates in position, a cutting tool is needed to separate the plate to recover the gel. This method is undesirable since the cutting tool can slip and cause gel damage. Clamping systems that use bolts require the use of tools such as screw drivers and wrenches to disassemble the cassettes and include several components that can be lost or damaged. Clamping systems using spring mechanisms have problems with uneven sealing due to uneven spring pressures on components that are not perfectly flat.

Accordingly, it would be desirable to provide a cassette for gel electrophoresis that does not introduce anomolies in the separation process, is easy to disassemble without tools or fixtures, minimizes the number of components forming the cassettes and minimizes gel damage during disassembly.

SUMMARY OF THE INVENTION

The present invention provides a gel electrophoresis cassette comprising two plates and two separators positioned between the plates. The separators are retained in position by means of an adhesive and a removable strip which extends the length of the separator. The strip is mechanically stronger than the adhesive. Subsequent to gel electrophoresis utilizing the cassette, the strips can be pulled manually away from the separators and plates, and, in the process, separate the adhesive from the separators and plates. The plates then can be manually removed from contact with the gel since the bond between (a) the adhesive and (b) the plates and separators has been broken by virtue of the strip removal.

BRIEF DESCRIPTION OF THE DRAWINGS

FIG. 1 is a plan view of the casette of this invention.
FIG. 2 is a side view of the cassette of FIG. 1.
FIG. 3 is a bottom view of the cassette of FIG. 1.

DESCRIPTION OF SPECIFIC EMBODIMENTS

Figure 4:
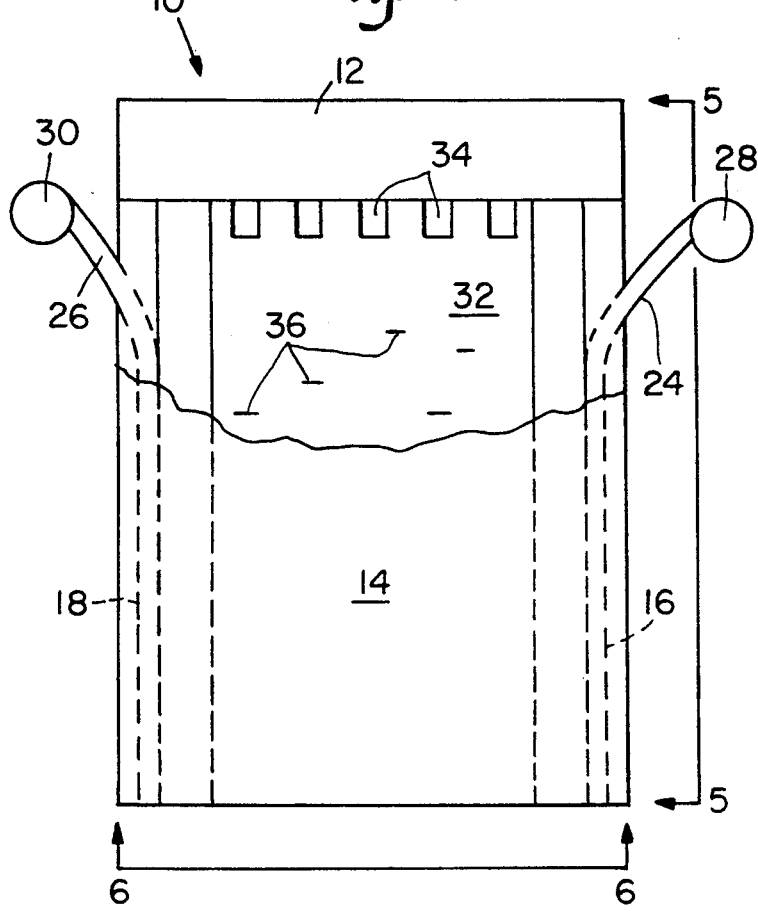
FIG. 4 shows a position of the strips after manual removal from the cassette of FIG. 1 has been inititated.

Referring to FIGS. 1, 2 and 3, the gel electrophoresis cassette of this invention 10 is shown. FIG. 2 is a side view of the cassette 10 of FIG. 1 in the direction of arrow 2. FIG. 3 is a bottom view of the cassette 10 of FIG. 1 in the direction of arrow 3. The cassette 10 is comprised of a back plate 12, a front plate 14 and two spacers 16 and 18. The spacers 16 and 18 and the plates 12 and 14 are retained together by means of adhesive strips 20 and 22. Solid strips 24 and 26 are embedded within and along the entire length of the adhesive strips and above the plate 14 so that a free end of the solid strip is exposed for grasping. Alternatively a tab 28 or 30 ca be attached to the solid strips 24 and 26 to promote ease of grasping. The electrophoresis gel 32 is positioned within the void volume defined by the plates 12 and 14 and the spacers 16 and 18. The gel 32 is provided with wells 34 which are molded into the gel 32 when it is formed in the void volume. The wells 34 house the samples which are to be separated within the gel 32.

Figure 5:
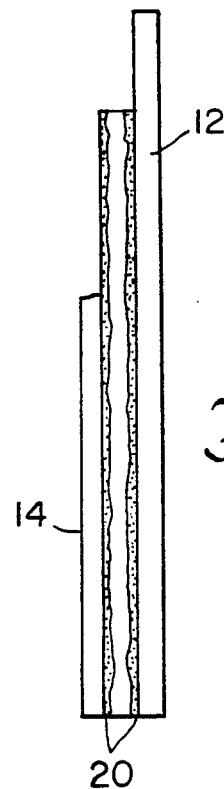
FIG. 5 is a side view of the cassette of FIG. 4 after the strips have been completely removed.
Figure 6:
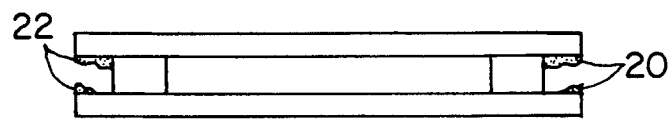
FIG. 6 is a bottom view of the cassete of FIG. 4 after the strips have been completely removed.

The function of this invention is described with reference to FIGS. 4, 5 and 6. FIG. 5 is a side view in the direction of arrow 5 of the cassette 10 of FIG. 4 after the solid strip 24 has been completely removed. FIG. 6 is a bottom view in the direction of arrow 6 after the solid strips 24 and 26 have been completely removed. As shown, the solid strips 24 and 26 are removed from the cassette 10 by grasping and pulling on the tabs 28 and 30 in order to tear the adhesive strips 20 and 22 along their entire length (see FIG. 5). In order to function in this manner, the solid strips 24 and 25 must be mechanically stronger than the adhesive 20 and 22 so that, upon pulling the strips 24 and 26, the adhesive strips 20 and 22 will tear as shown, for example, in FIGS. 5 and 6. While some portion of the adhesive remains adhered to a plate, or spacer, after tearing, there is insufficient adhesion which permits manual separation of the plates and spacer so that the gel can be recovered and the separated samples 36 analyzed.

The strip can be formed of any solid, electrically nonconductive material of suitable mechanical strength such as a polymeric material. The adhesive, preferably is a room temperature vulcanizable (RTV) adhesive or ultraviolet light (UV) curable adhesive. Representative suitable adhesives include silicone or epoxy based adhesives since these adhesives are relatively soft when cured and can be easily torn when the solid strips are removed. The adhesive should have a Durometer (Shore A) of between about 45 and 70, preferably between about 55 and 65. In addition, these adhesives are easily applied, remain in place during curing and remain integral with the cassette for long periods, typically greater than one year. In addition, these adhesives are compatible with the buffers used in electrophoresis.

We claim:

1. A cassette for conducting electrophoresis which comprises:
   a first flat plate having two side edges,
   a second flat plate having two side edges,
   a first spacer positioned inward slightly away from a side edge of said first flat plate and away from a side edge of said second flat plate to form a first small space between said plates,
   a second spacer positioned inward slightly away from a side edge of said first flat plate and away from a side edge of said second flat plate to form a second small space between said plates,
   a void volume adapted to retain a gel defined by said first flat plate, said second flat plate, said first spacer and said second spacer,
   a first strip positioned within said first small space and retained therein with a soft adhesive,
   a second strip positioned within said second small space and retained therein with said soft adhesive,
   said soft adhesive having a Durometer (Shore A) hardness between about 45 and 70 and being mechanically weaker than said first strip and said second strip to permit said first strip and said second strip to be removed from said first small space and said second small space respectively.

2. The cassette of claim 1 wherein said void volume is filled with an electrophoresis gel.

3. The cassette of claim 1 wherein a first tab is secured to one end of said first strip and a second tab is secured to one end of said second strip.

4. The cassette of claim 2 wherein a first tab is secured to one end of said first strip and a second tab is secured to one end of said second strip.

5. The cassette of claim 2 wherein a plurality of wells extend from a top surface of said gel and into said gel.

6. The cassette of claim 5 wherein a first tab is secured in one end of said first strip and a second tab is secured to one end of said second strip.

7. The cassette of claim 1 wherein said adhesive is a silicone based adhesive.

8. The cassette of claim 2 wherein said adhesive is a silicone based adhesive.

9. The cassette of claim 5 wherein said adhesive is a silicone based adhesive.

10. The cassette of claim 1 wherein said adhesive is an epoxy based adhesive.

11. The cassette of claim 2 wherein said adhesive is an epoxy based adhesive.

12. The cassette of claim 1 wherein said adhesive is an epoxy based adhesive.

13. The cassette of claim 1 wherein said adhesive has a Durometer (Shore A) hardness between about 55 and 65.

14. The cassette of claim 2 wherein said adhesive has a Durometer (Shore A) hardness between about 55 and 65.

15. The cassette of claim 5 wherein said adhesive has a Durometer (Shore A) hardness between about 55 and 65.

* * * * *